United States Patent
Foster

(10) Patent No.: US 6,994,090 B1
(45) Date of Patent: Feb. 7, 2006

(54) UNDERARM SUPPORT

(76) Inventor: LeBaron A. Foster, 2172 St. Stephens Rd., Mobile, AL (US) 36617

( * ) Notice: Subject to any disclaimer, the term of this patent is extended or adjusted under 35 U.S.C. 154(b) by 0 days.

(21) Appl. No.: 10/284,233

(22) Filed: Oct. 29, 2002

(51) Int. Cl.
*A61G 15/00* (2006.01)

(52) U.S. Cl. ...................... 128/845; 128/875; 128/876; 602/20; 2/53

(58) Field of Classification Search .............. 128/845, 128/875, 876, 878; 602/4, 36, 78, 20; 2/53, 2/54, 55, 56, 57, 58
See application file for complete search history.

(56) References Cited

U.S. PATENT DOCUMENTS

| | | | | |
|---|---|---|---|---|
| 5,235,975 A | * | 8/1993 | Gang et al. ................. | 128/875 |
| 5,248,293 A | * | 9/1993 | Hubbard et al. ............ | 128/875 |
| 5,263,496 A | * | 11/1993 | Cherniak .................... | 128/876 |
| 5,314,404 A | * | 5/1994 | Boughner et al. ........... | 602/36 |
| 5,405,313 A | * | 4/1995 | Albin .......................... | 602/20 |
| 5,816,251 A | * | 10/1998 | Glisan ......................... | 126/845 |
| 5,865,180 A | * | 2/1999 | Sigfrid ....................... | 128/845 |
| 5,906,205 A | * | 5/1999 | Hiebert ....................... | 128/845 |
| 6,435,185 B1 | * | 8/2002 | Schimpl ..................... | 128/845 |

* cited by examiner

*Primary Examiner*—Fadi H. Dahbour

(57) ABSTRACT

The invention is an underarm support for one or both arms having a pad which fits under the arm of the user, preferably in the arm pit, flexible and of sufficient diameter under compression at that area to open the arm outward for greater blood flow and to more correctly position the arm. In order to assist in lifting the arm at the armpit and to secure the pad in place, a strap fits over one or both shoulders and passes around the torso from the should strap above the underarm. In the preferred embodiment, the strap fits over the shoulder directly above the arm to be lifted. A second strap travels around the torso of the user in order to hold the pad in place. The pad is preferably flexible at least the same width as the underarm of the user.

12 Claims, 6 Drawing Sheets

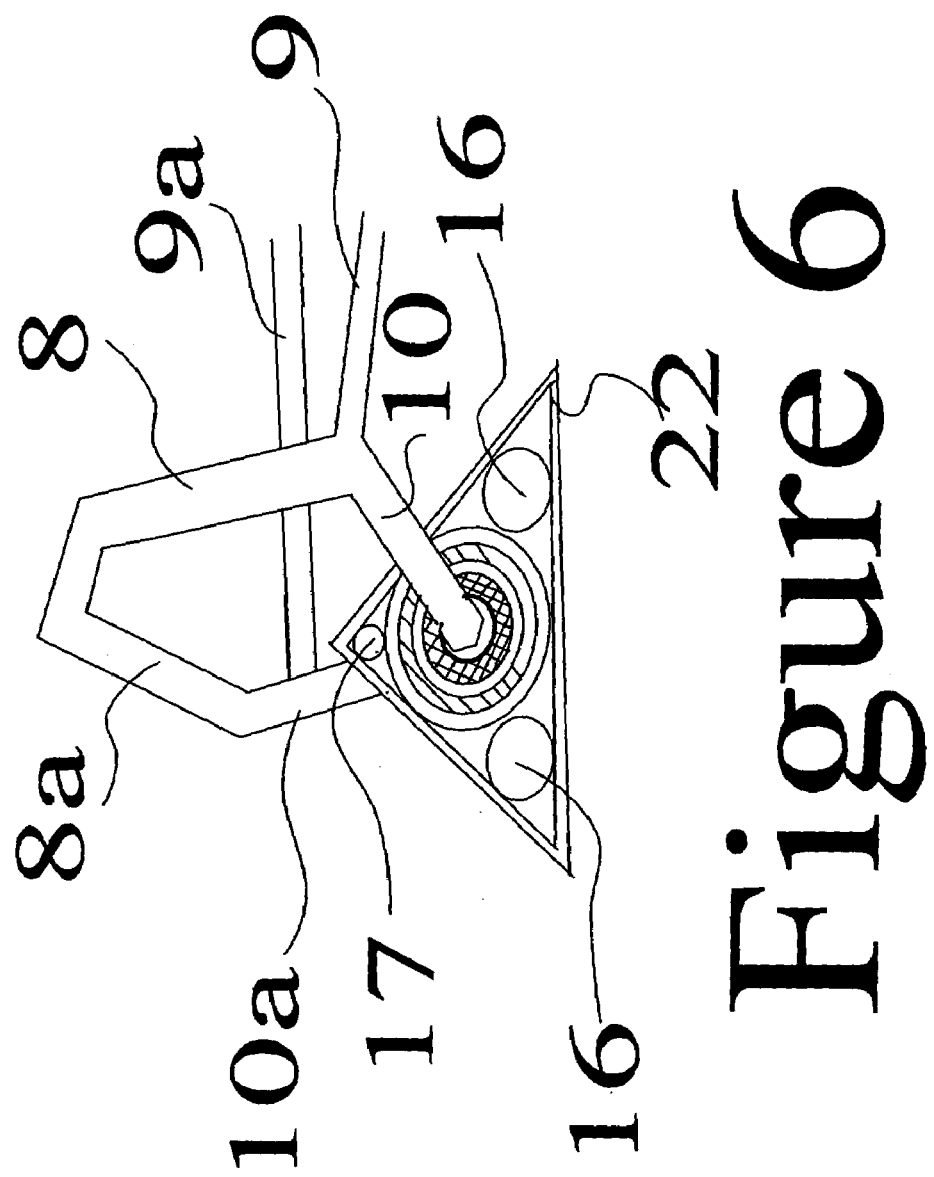

UNDERARM SUPPORT

BACKGROUND OF INVENTION

1. Field of the Invention

The invention is in the field of body supports. More particularly, the invention pertains to body supports fitting under the arm of the user and supported at the shoulder.

2. Prior Art

It is known in the prior art to support broken or damaged appendages.

GENERAL DISCUSSION OF THE INVENTION

The invention is a support which can go under one or both arms of the user in order to raise the arm to increase circulation.

This can be important for a number of conditions. For stroke victims there is often a slumping of one side or the other and this particular invention offsets that for a greater blood flow to the member which would otherwise have a restricted blood flow and restricted nerve passages as a result of being tilted downward and the associated compression of the tissues.

It can also be used for arthritic conditions and other conditions where blood flow to the extremities is a problem.

Other conditions where this would be helpful might include back injuries where there was sloping of one side or the other, however marginal or where the nerve or blood supply is restricted as a result of an injury. The invention can serve to enhance blood supply and nerve conduction for a variety of users.

It is noted that while the pad used is as more or less round in these embodiments that a variety of shapes might be used for different users as well as a variety of widths in order to fit different age and different size users.

In some instances is might be better to have a wedge shape or in some instances may be better to have a more squared shape.

The basic parameters of the invention are to have an underarm cushion which lifts out the arm or lifts up at the armpit. While there are several methods of accomplishing this the method taught herein is felt to be superior for several reasons which will be clear from the disclosure herein.

Because of the several requirements which are accomplished utilizing this invention, many of the parts serve multiple functions.

These and other objects and advantages of the invention will become better understood hereinafter from a consideration of the specification with reference to the accompanying drawings forming part thereof, and in which like numerals correspond to parts throughout the several views of the invention.

BRIEF DESCRIPTION OF THE DRAWINGS

FIG. 6 shows an alternately shaped pad with removable spacers.

For a further understanding of the nature and objects of the present invention, reference should be made to the following detailed description taken in conjunction with the accompanying drawings in which like parts are given like reference numerals and wherein:

DETAILED DESCRIPTION OF THE PREFERRED EXEMPLARY EMBODIMENTS

Figure 1:
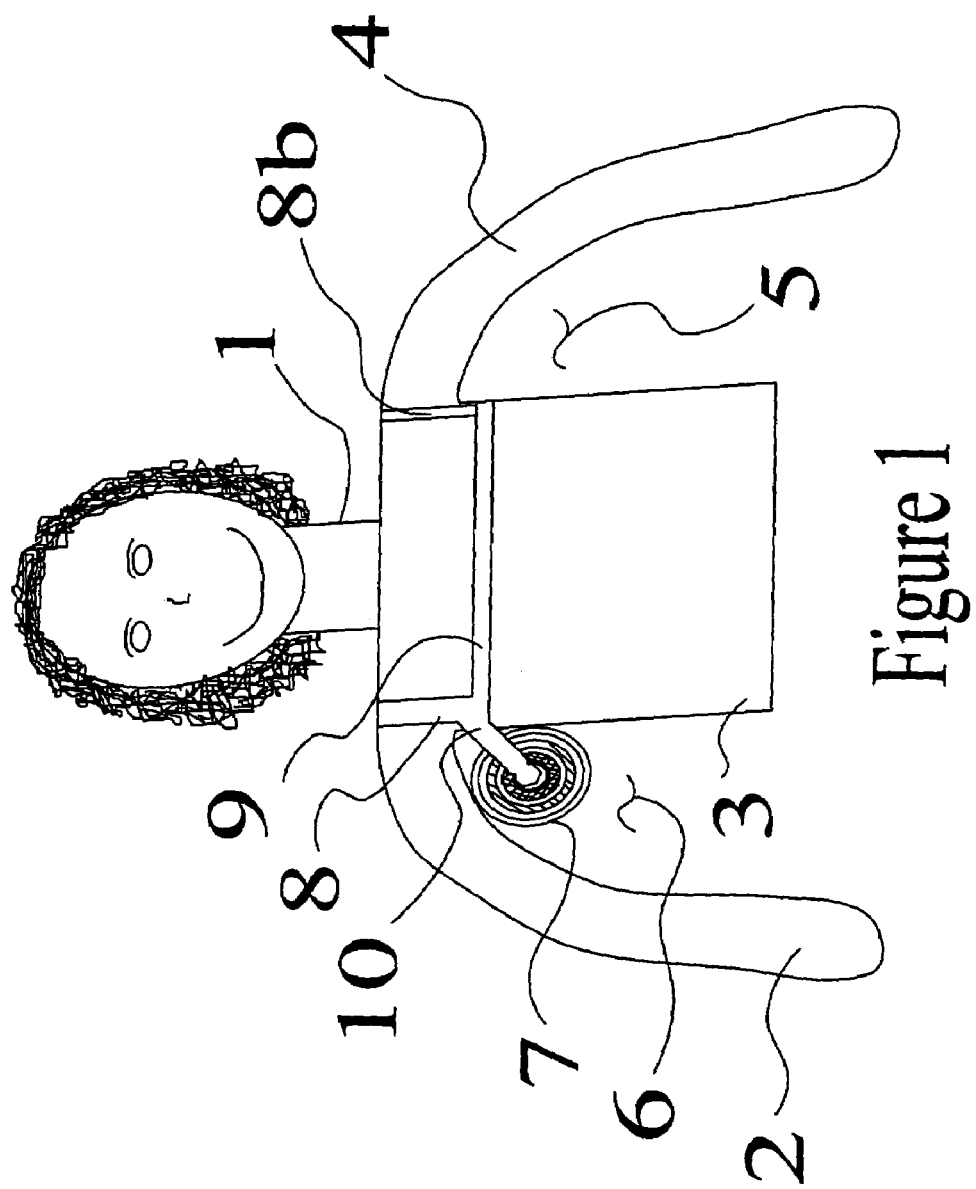
FIG. 1 is a view of the device on a body.
Figure 4:
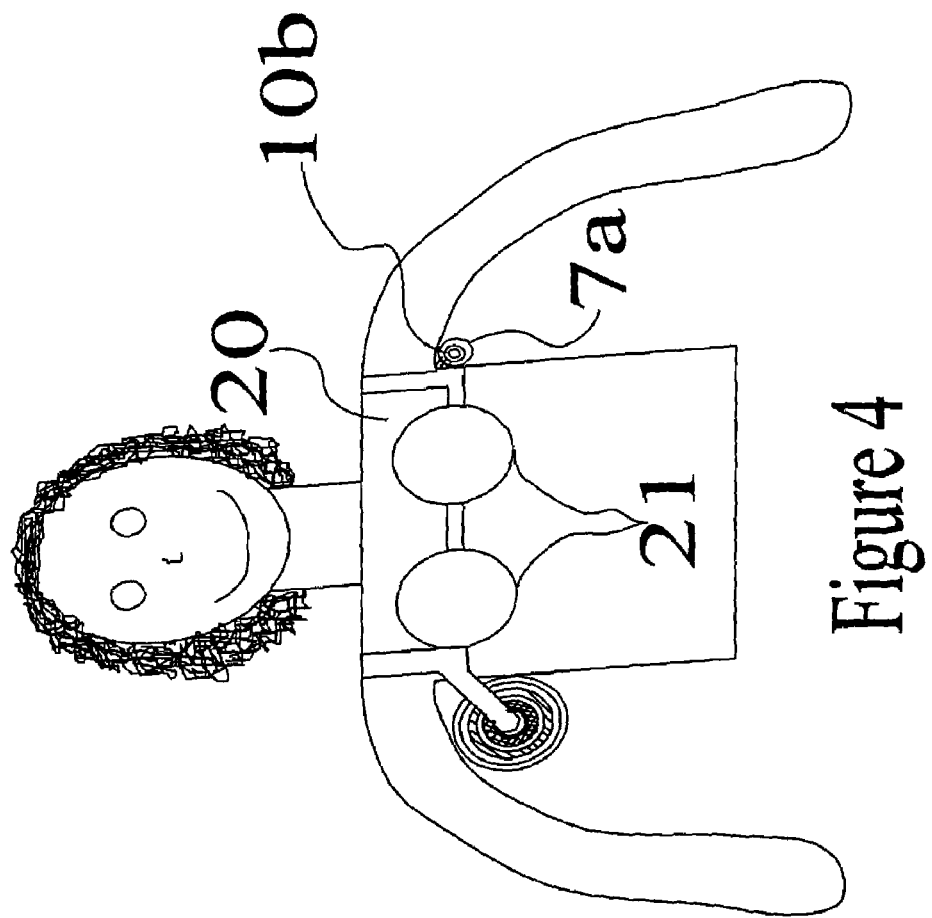
FIG. 4 shows 2 pads on either side of a body and incorporated into a bra.

As can best be see by reference to FIG. 1 the invention is used by a user 1 having a low arm 2 (defined as the arm where the support is needed), a torso 3, an high arm 4 (defined as the arm opposite the low arm). In some embodiments, as shown in FIG. 4, there may be two pads 7 and 7a under each arm 2 and 4, respectively, although this is not typically the case.

The arms could just as easily be referred to as the left and right arm, but for purposes of understanding the invention, the low and high arm designations are made.

There is a space 5 between the torso 3 and the high arm 2. There is also a space 6 between the torso 3 and the low arm 2. These spaces are referred to typically as the underarms. Since the pad 7 fits within the underarm and contacts the torso 3 and arm 2 in the general area where they connect, the definitions need not be characterized with any particular language.

Figure 2:
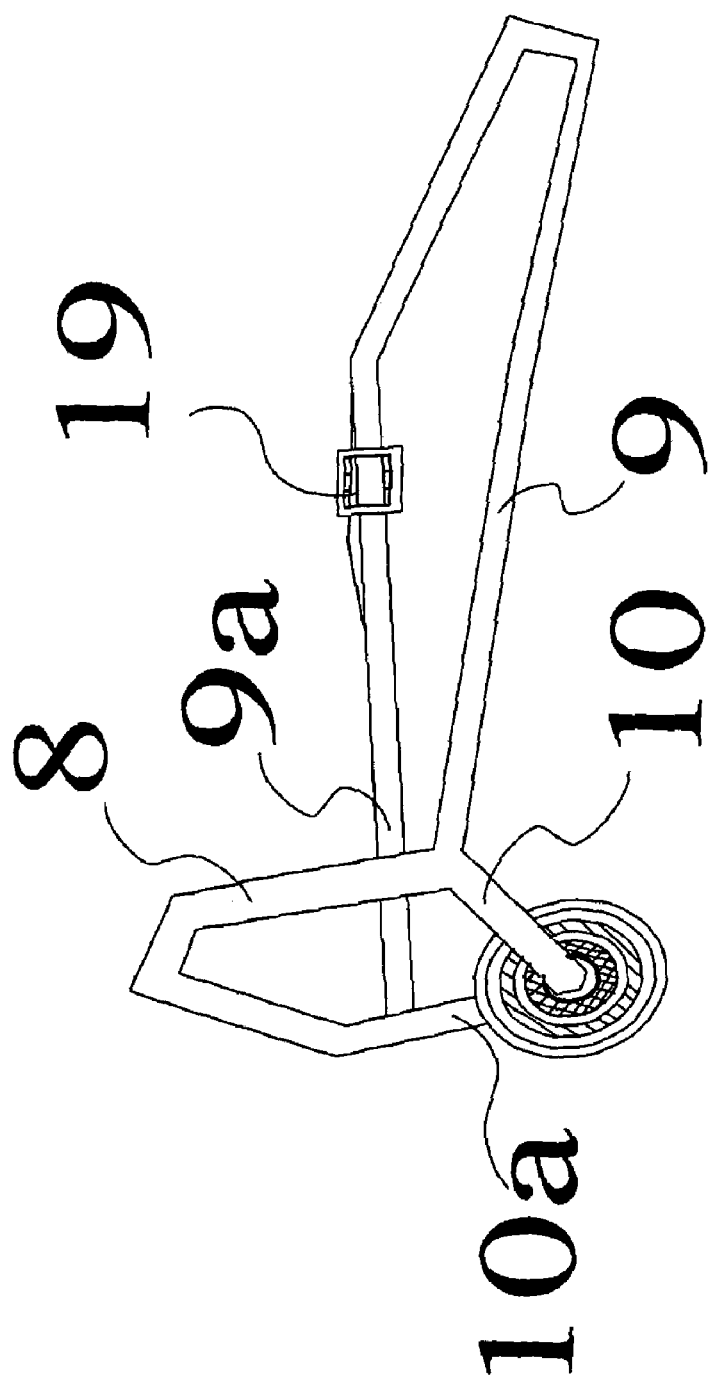
FIG. 2 shows a view of the device off of the body from FIG. 1.
Figure 3:
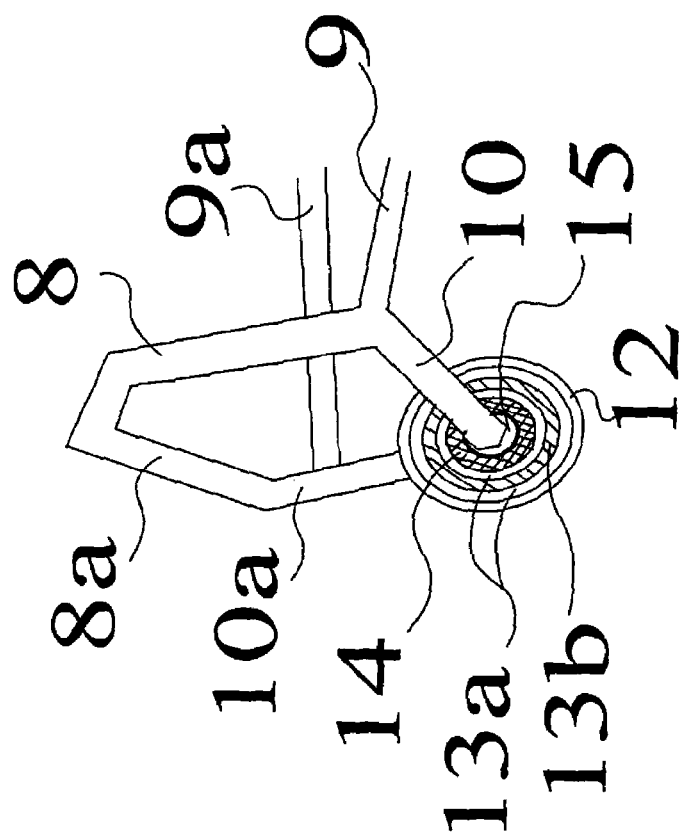
FIG. 3 shows a close up view of the pad from FIG. 1.

A pad 7 which is described in more detail in reference to FIGS. 2 and 3 fits in the space 6 at the juncture 11 of the arm and shoulder of the user. In the preferred embodiment the pad 7 defines a hole 15 through which the connection strap passes. The pad 7 which is the underarm support is preferably in layers, at least one of which is soft rubber with at least one cover of elasticized fabric and machine washable.

In FIG. 3, the pad 7 is shown as defining the hole 15 defined by a semi-rigid or rigid reinforcing layer 14 which helps the pad 7 maintain it's shape. Around this is at least one, and in this example, two flexible layers 13a and 13b of rubber material, a protective layer 18 and finally the cover 12. The protective layer to protect and separate the user from the rubber is optional. Also, one or more of the flexible layers may be removable to increase or decrease the total diameter of the pad 7.

As can best be seen by reference to FIGS. 2 and 3 the strap 10 goes through the hole 15 in the pad 7. The pas is comprised of an outer layer 12 which is preferably absorbent and may be rubber or other cushioning material and within that is yet another layer which is a reinforcing layer 14 which serves the purpose of helping the invention to maintain its shape.

The point of attachment of the chest strap 9 to the connecting strap 10 shows where the connecting strap 10 changes to the shoulder strap 8. While these are numbered different, they are preferably different sections of a continuous strap which are identified separately to more clearly show the offset of the chest strap 9 which is accomplished to hold the pad 7 more comfortably in place.

The pad may be tightened or even moved along the straps to provide pressure where pressure is therapeutic.

The point near or at where the shoulder strap 8 enters the hole 15, the arrangement of these straps serves to hold the position of the pad 7 and prevent the pad 7 from sliding out of a comfortable spot under the armpit.

The shoulder strap 8 which is preferably made of elastic material holds the pad 7 in place and also serves to provide some lift pulling the arm 2 up. On FIG. 3 the part of the strap 8 which passes over the back of the user is designated as strap section 8(a). The portion of the shoulder strap 9 which passes along the back of the user 1 is designated as strap 9a.

FIG. 2 shows that strap 9a has a buckle 19 which allows the length of the chest strap 9 to be taken in to keep the device tight.

Both straps 8 and 9 are preferably flexible so that they fit snugly.

The fit is not overly tight and little lift is given because no circulation changes are desirable but it may be tightened and provide more lift and a tighter fit if necessary.

A second strap 8b going over the opposite shoulder from the strap 8 may be provided in order to provide greater lift and provide more distribution. As shown in FIG. 4, this strap 8b may hold another pad 7a which may be larger, smaller or the same size as pad 7.

In the preferred embodiment there is single strap 8 and the user may slide this over his arm while putting the pad 7 in place.

A second elastic chest strap 9 may go over the head of the user and be pulled so that it goes around the user's torso or chest 3. This strap 9 and shoulder strap 8 are attached on either side to the pad 7 to hold the pad in place as the user moves about.

Since the main purpose of these straps is to maintain the position of the pad 7 so that they may be fairly loose and elastic.

The shoulder strap holds the pad 7 at the proper location under the shoulder by fitting over the shoulder and the chest strap serves to keep the pad 7 from sliding out from under the arm and up.

Both straps may be adjustable in the size. Both straps are preferably elastic. The location of the buckle 19 may be movable and even the length and diameter of the pad may be adjustable or may involve changing out pads of different sizes to make the device more comfortable to use.

As can be shown by reference to FIGS. 1, 2 and 3 between where the shoulder strap 8 intersects with the chest strap 9 and rear strap 9a there is a connecting strap 10 which actually passes through an opening, hole 15, in the center of the pad 7. While in the preferred embodiment it passes through the pad 7, it can be seen to anyone skilled in the art that is would be possible to have the shoulder strap 8 attached on either side of the pad 7, although that does not give the amount of support that is available utilizing the system described in the preferred embodiment.

The straps are flexible, but one or more may be made inflexibly in order to stiffen the product and in such a case, the strap may be padded to prevent chafing which is accomplished by having the material of the pad, and potentially the straps, covered by a soft cloth absorbent layer 12.

FIG. 4 shows how the device may be used with a bra 20. Here the chest strap 9 is broken with cups 21 as is known in the prior art. The connecting straps 10 have been added where the shoulder and chest straps meet to properly hold and center two pads 7 and 7a. While two pads 7 and 7a are shown here, only one pad is used in the preferred embodiment. The connecting strap centers the shoulder straps and chest straps between the underarm of the user and the neck of the user as shown in FIG. 1.

Pad 7a in this FIG. 4 is stitched to the connecting strap 10b to show where a center opening in the pad is not required.

Figure 5:
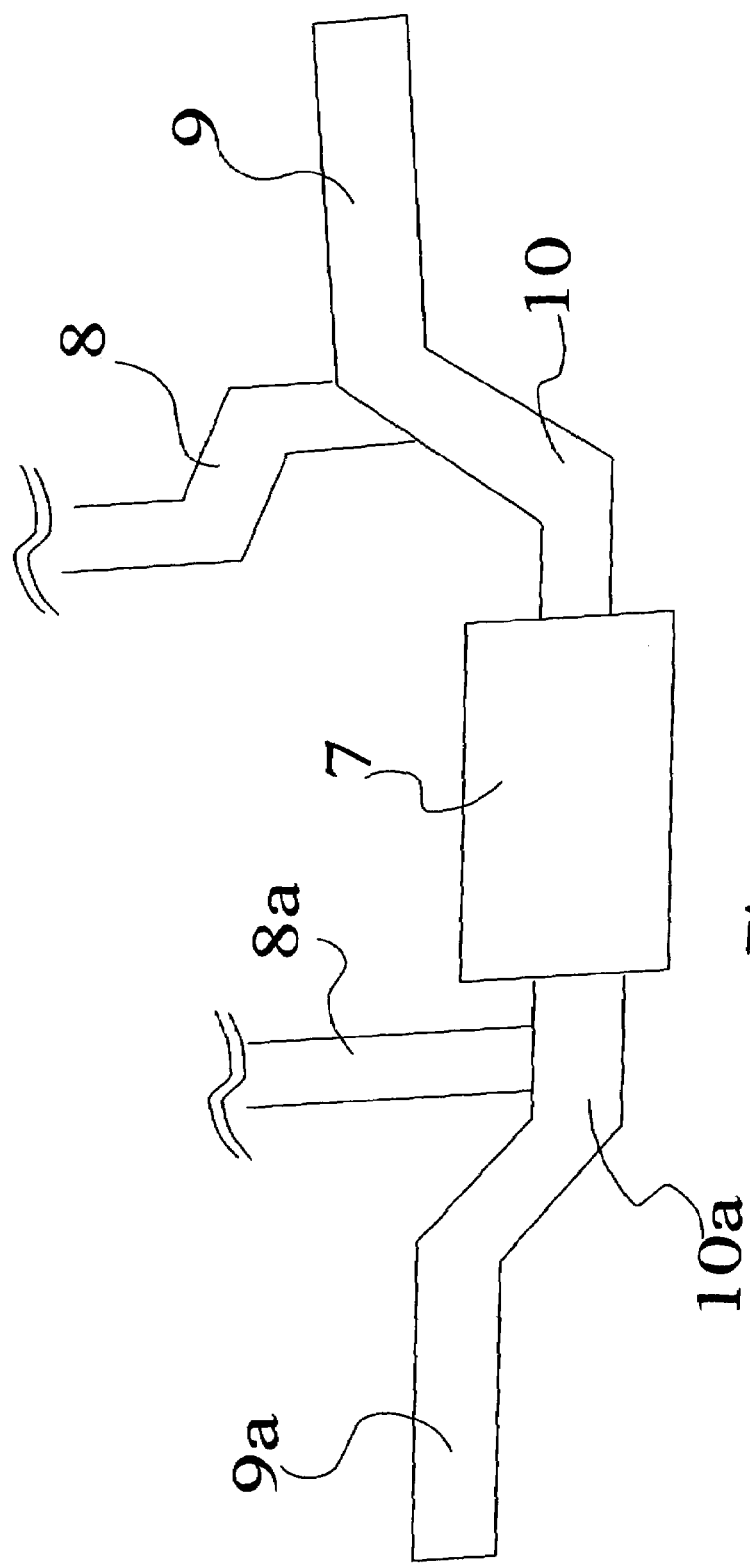
FIG. 5 shows a side view of the pad and retaining straps.

FIG. 5 shows a side view of the pad and retaining straps. The length of the tube defined by the pad 7 may be between three and 7 inches. While the preferred embodiment has a stiff reinforcing layer 14, a more flexible pad 7 could be longer, even being continuous around the torso although this is not within the scope of the preferred embodiment. The diameter of the tube shown in FIG. 4 may be between ¼ inch and 4 inches in diameter.

The size and exact location of the connecting straps 10 and 10a may be varied as shown on FIG. 5 where centering above the shoulder is unnecessary.

FIG. 6 shows an alternately shaped pad with removable spacers. In this case, there are large spacers 16 and a smaller spacer 17 which sizes allow for the shape of the flexible, elastic outer layer 22 to change. This also allows the size of the triangular pad 7 to be changed slightly.

If the spacers were attached to the strap 10, then multiple pads would be in place instead of a single composite pad 7.

Because many varying and different embodiments may be made within the scope of the inventive concept herein taught and because many modifications may be made in the embodiment(s) herein detailed in accordance with the descriptive requirements of the law, it is to be understood that the details herein are to be interpreted as illustrative and not in a limiting sense.

What is claimed is:

1. An underarm circulation support device for a user with a body having a first arm, a torso and an arm pit at the juncture of the first arm and the torso and a second arm, torso and arm pit comprising:
   a) a spacing means having a front and the front of the user and a rear at the back of the user for separating the arm and the torso at the arm pit;
   b) a securing means for holding the spacing means at the arm pit of the user and wherein the spacing means is flexible and wherein the spacing means further comprises at least one pad and an absorbent cover and wherein the spacing means comprises a length and wherein the spacing means comprises a pad and wherein the pad defines a length between three inches and six inches and wherein the pad is cylindrical along its length and wherein wherein the securing means comprises a strap which is continuous through the pad and travels around shoulder and around the torso of the user.

2. An underarm circulation support device for a user with a body having an a first arm, a torso and an arm pit at the juncture of the first arm and the torso and a second arm, torso and arm pit comprising:
   a) a spacing means having a front and the front of the user and a rear at the back of the user for separating the arm and the torso at the arm pit;
   b) a securing means for holding the spacing means at the arm pit of the user and wherein the securing means comprises at least two straps, being a shoulder strap and a chest strap and wherein the shoulder strap runs between spacing means and the shoulder above underarm and wherein the chest strap runs from the shoulder strap on the front of the spacing means across the chest of the user under the second arm of the user and along the back of the user to attach to the shoulder strap on the rear of the spacing means.

3. The device of claim 2 wherein at least one of the at least two straps is elastic.

4. The device of claim 3 wherein at least one of the straps is adjustable in length.

5. The device of claim 2 wherein at least one of the straps is inflexible.

6. The device of claim 2 wherein the pad further comprises a spacer means between chest strap and shoulder strap and the pad to disburse stress above the underarm.

7. The device of claim 2 wherein the shoulder strap and chest strap centers between the underarm of the user and the neck of the user.

8. The device of claim 2 wherein the pad has variable diameter.

9. A method of providing circulation between the chest and arm of a user with an underarm comprising the steps of:
   a) determining the amount of spacing at the underarm of the user is desired;
   b) preparing a spacing means for defining the amount of spacing determined in the preceding step;
   c) securing the spacing means at the underarm of the user without encumbering any other attachments to the body other than with a shoulder strap and a strap which is continuous around the torso of the user.

10. The method of claim 9 wherein the step of preparing a spacing means comprises preparing a stiff spacer with a padded exterior and an absorbent outer cover.

11. The method of claim 9 wherein the step of securing the spacing means comprises the step of securing the spacing means above the shoulder of the user and across the chest of the user.

12. The method of claim 11 wherein the step of securing further comprises the step of securing the spacing means across the chest further comprises the step of securing the spacing means across the chest of the user above the underarm.

* * * * *